(12) United States Patent
Li et al.

(10) Patent No.: US 11,774,352 B1
(45) Date of Patent: Oct. 3, 2023

(54) APPARATUS AND METHODS FOR CONTROLLED DRUG WASTE DIVERSION DETECTION

(71) Applicants: Qun Li, Newark, DE (US); Sean Xiaolu Wang, Wilmington, DE (US)

(72) Inventors: Qun Li, Newark, DE (US); Sean Xiaolu Wang, Wilmington, DE (US)

( * ) Notice: Subject to any disclaimer, the term of this patent is extended or adjusted under 35 U.S.C. 154(b) by 68 days.

(21) Appl. No.: 17/702,860

(22) Filed: Mar. 24, 2022

(51) Int. Cl.
| | |
|---|---|
| *C12N 15/10* | (2006.01) |
| *B01L 3/00* | (2006.01) |
| *G01N 35/10* | (2006.01) |
| *B01L 3/02* | (2006.01) |
| *B33Y 80/00* | (2015.01) |
| *B33Y 10/00* | (2015.01) |
| *B33Y 70/00* | (2020.01) |
| *G01N 33/53* | (2006.01) |
| *G01N 21/33* | (2006.01) |
| *G01N 33/15* | (2006.01) |
| *G01N 21/31* | (2006.01) |

(52) U.S. Cl.
CPC ............ *G01N 21/33* (2013.01); *G01N 33/15* (2013.01); *G01N 2021/3125* (2013.01); *G01N 2021/3133* (2013.01)

(58) Field of Classification Search
CPC .................. G01N 21/33; G01N 33/15; G01N 2021/3125; G01N 2021/3133
See application file for complete search history.

(56) References Cited

U.S. PATENT DOCUMENTS

2005/0077476 A1\* 4/2005 Poteet .................... G16H 10/40
250/461.1

\* cited by examiner

*Primary Examiner* — Jennifer Wecker
*Assistant Examiner* — Oyeleye Alexander Alabi (57) ABSTRACT

This invention provides a UV spectroscopy apparatus and method for controlled drug waste diversion detection. The spectroscopy apparatus employs sample cells which have optimized optical path length such that the measured maximum absorbance of the drug is less than the detection limit of the system. Hence the full unsaturated absorption spectrum of the drug is revealed in the UV wavelength region from 230 nm (or even down to 195 nm) to 400 nm. This full spectrum analysis improves the specificity for drug identification and the accuracy for drug concentration verification. The spectral library of the apparatus comprises the spectra of preservative-free controlled drugs, common excipients, as well as typical diluents, which enables the identification of controlled drugs from different manufacturers and/or diluted with different types of diluents.

11 Claims, 7 Drawing Sheets

APPARATUS AND METHODS FOR CONTROLLED DRUG WASTE DIVERSION DETECTION

GOVERNMENT FUNDING

This invention was made with government support under contract number 75N95021C00030 awarded by National Institutes of Health. The government has certain rights in the invention.

FIELD OF THE INVENTION

This invention relates to apparatus and methods for controlled drug waste diversion detection.

BACKGROUND OF THE INVENTION

Narcotic abuse is the most rapidly growing public health concern in the United States. The micro-environment for controlled drug diversion within healthcare facilities is particularly concerning, as caregivers are largely granted easy and unabated access to prescription drugs within the confines of ineffective controls. Diversion can be easily committed by covertly substituting another clear liquid for the drug prior to a witnessed waste. In fact, healthcare providers are five-fold more likely to suffer from opiate abuse than the general public. While some hospitals have introduced a system of pharmacy return and qualitative testing, or even send away HPLC testing, few hospitals have the personnel or budget to administrate such a costly, time-consuming process that is still wholly ineffective.

The present invention utilizes ultraviolet (UV) spectroscopy for fast onsite detection of controlled drug waste diversion as common controlled drugs are strong UV light absorbers with high optical absorption even at low concentration levels. The measurement can be completed within a few seconds versus 10-30 minutes for HPLC methods. However, there are several obstacles which need to be overcome for the successful implementation of the technology. First, traditional sample cells or cuvettes for UV absorption measurement have a relatively long optical path length of 10 mm. At such a long path length, the absorbance of the drug at its absorption peak is often too high such that the obtained UV absorption spectrum is saturated near the absorption peak (especially at wavelengths of <300 nm) since most of the spectroscopy system can only handle absorbance values of less than 4. As a result, one has to resort to the tail of the absorption bands for drug identification and concentration verification. This greatly limits the specificity of the UV spectroscopy technology for drug identification. Second, dugs from different manufacturers may have different excipients, which are used as solvent, preservative, stabilizer, antioxidant, or function for isotonicity and/or for pH adjustment. These excipients may contribute to the UV absorption such that drugs from different manufacturers exhibit different spectral shapes. This adds to the complexity of drug identification based on UV spectroscopy. Third, certain controlled drugs are provided in a concentrated form and require dilution before usage. The types of diluents used for dilution may also affect the spectral shape of the diluted drug.

SUMMARY OF THE INVENTION

It is thus the goal of the present invention to solve the above-mentioned problems and provide an improved UV spectroscopy apparatus and method for controlled drug waste diversion detection. The spectroscopy apparatus employs sample cells which have optimized optical path length such that the measured maximum absorbance of the drug is less than the detection limit of the system. Hence the full unsaturated absorption spectrum of the drug is revealed in the UV wavelength region from 230 nm (or even down to 195 nm) to 400 nm. This full spectrum analysis improves the specificity for drug identification and the accuracy for drug concentration verification. The spectral library of the apparatus comprises the spectra of preservative-free controlled drugs, common excipients, as well as typical diluents, which enables the identification of controlled drugs from different manufacturers and/or diluted with different types of diluents.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Before describing in detail embodiments that are in accordance with the present invention, it should be observed that the embodiments reside primarily in combinations of method steps and apparatus components related to a UV spectroscopy apparatus and method for controlled drug waste diversion detection. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1:
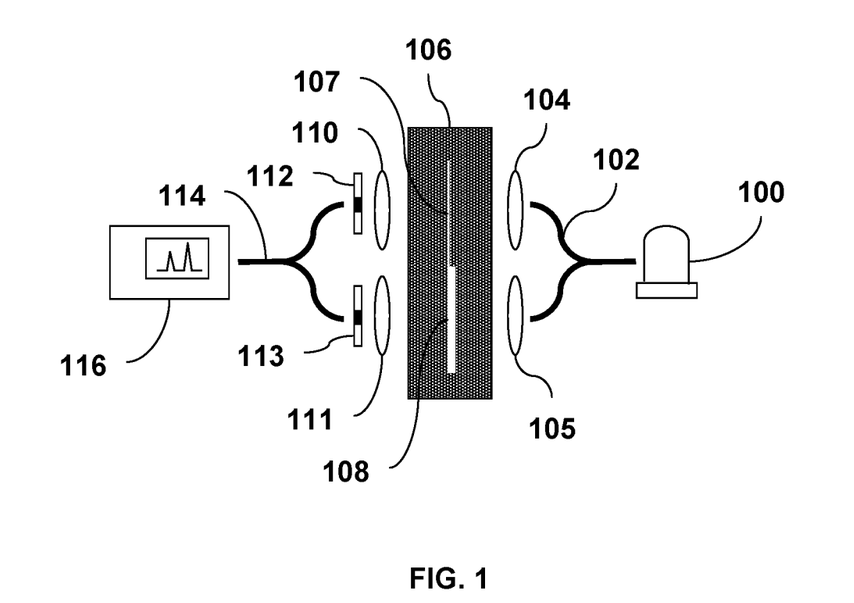
FIG. 1 illustrates an exemplary embodiment of the improved UV spectroscopy apparatus for controlled drug waste detection.

An exemplary embodiment of the improved UV spectroscopy apparatus is shown in FIG. 1. The UV spectroscopy apparatus comprises a UV light source 100, which is preferably a high power Deuterium lamp producing broadband continuous UV emission in the wavelength range from 185 nm to 400 nm. The output UV light from the light source 100 is coupled into a bifurcated fiber bundle 102 and split into two parts, one of which is collected and collimated by optical lens 104 and the other by optical lens 105. The collimated UV light transmits through a customized cuvette 106, which has two interconnected fluid chambers 107 and 108. The upper chamber 107 has a shorter optical path length of e.g., 0.1 mm and the lower chamber 108 has a longer optical path length of e.g., 0.5 mm. The UV light is partially absorbed by the drug waste sample in the two chambers 107 and 108. The transmitted UV light from the two chambers 107 and 108 is collected and focused by another pair of optical lenses 110 and 111 into another bifurcated fiber bundle 114, respectively, which is then combined and delivered into an optical spectrometer 116 for spectral analysis. A pair of optical shutters 112 and 113 is inserted between the bifurcated fiber bundle 114 and the optical lenses 110 and 111, respectively for controlling which of the transmitted UV light from the two chambers 107 and 108 is delivered into the optical spectrometer 116. In this exemplary embodiment, the optical spectrometer 116 has wavelength coverage from 185 nm to 400 nm, matching with the emission spectrum of the UV light source 100. In other variations of the invention, the Deuterium lamp may be replaced with other types of UV light sources such as LEDs, lasers, or supercontinuum light sources.

The UV spectrum of the controlled drug waste sample is measured in two steps. In the first step, the cuvette 106 is filled with a reference liquid, which is preferably pure water as water is used as the solvent for most of the controlled drugs. The spectrum of the transmitted UV light through the reference liquid is collected to obtain a first spectrum. In the second step, the cuvette 106 is filled with the drug waste sample and the transmitted UV light through the drug waste sample is collected to obtain a second spectrum. The second spectrum is then divided by the first spectrum to calculate an absorption spectrum of the drug waste sample in reference to the reference liquid (pure water has almost no UV absorption at wavelengths of >190 nm). The library spectra of controlled drugs, common excipients and diluents can be collected in a similar manner. The absorption spectrum obtained in this manner is independent of the instrument (light source, spectrometer, etc.) and is only affected by the path length and material (typically UV grade fused silica) of the cuvette 106. Hence the measured spectral library can be easily transferred from one instrument to another. This approach also minimizes the noise caused by fluctuation in intensity of the light source and response of the optical spectrometer.

As disclosed before, certain controlled drugs exhibit strong UV absorption at high concentration levels, which cause the measured UV absorption spectrum to saturate in a large portion of the UV wavelength region (especially at wavelengths of <300 nm). Certain excipients (such as methylparaben which is used as preservative in some Hydromorphone products) also exhibit strong UV absorption at their typical concentration levels, which causes the measured UV absorption spectrum of the corresponding controlled drug to saturate even at relatively low concentration levels for the active ingredients. As the saturated spectrum loses its spectral features, this will pose a challenge for the correct identification of the controlled drug. The two path length design of the cuvette 106 helps to solve this issue. The chamber 107, which has a short optical path length, makes it possible to measure almost all types of controlled drugs at maximum clinical concentration levels with no spectral saturation issue in the full UV spectral region of interest (e.g. from 230 nm to 400 nm). The chamber 108, which has a long optical path length, enables the measurement of certain controlled drugs, such as Fentanyl and Sufentanil, which are used at low concentration levels under typical clinical settings. Beyond the customized cuvette as show in FIG. 1, the multiple path length design can be realized in other manners, for example, by employing two separate sample cells (cuvettes) which have different optical path lengths, or by varying the incident angle of the UV light to the cuvette to change the path length.

The UV spectroscopy apparatus is equipped with a spectral library comprising the collected spectra of preservative-free controlled drugs as well as commonly used excipients and diluents for the identification of drug wastes from different manufacturers and/or diluted with different types of diluents. The spectral library can be stored locally in the UV spectroscopy apparatus or remotely on a cloud server. Here the term 'preservative-free controlled drugs' refer to controlled drugs having the least number of excipients such that their UV absorption in the spectral region of interest (e.g., 230 nm-400 nm) is mainly caused by the active ingredient. These preservative-free controlled drugs are available from some manufacturers. For certain controlled drugs which always come with excipients having interfering UV absorption, the 'preservative-free' version of their spectra can be obtained by measuring both the drug spectrum and the related excipient spectra and then calculating a preservative-free spectrum from the drug spectrum and the excipient spectra.

Figure 2:
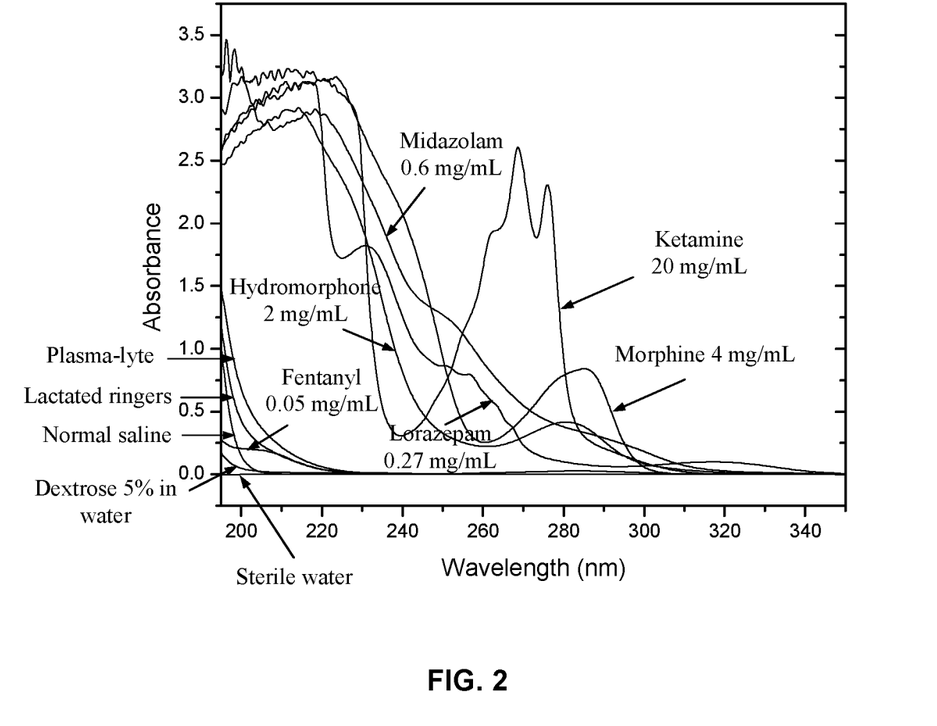
FIG. 2 shows an exemplary UV absorption spectrum library of preservative-free controlled drugs and typical diluents.
Figure 3:
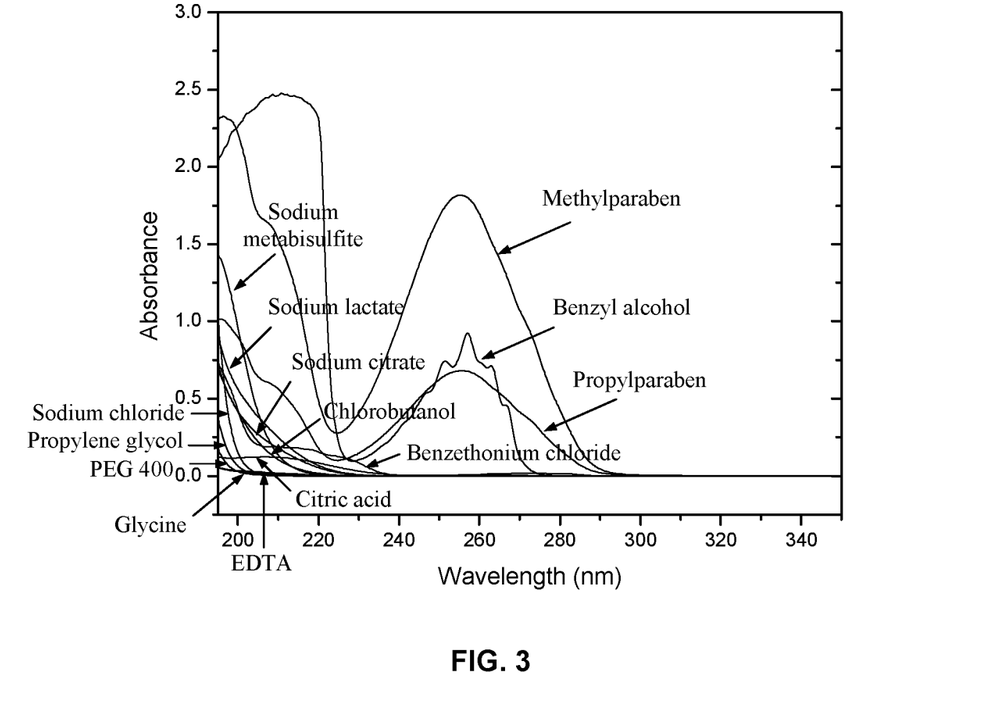
FIG. 3 shows an exemplary UV absorption spectrum library of common excipients in controlled drugs.

As one exemplary embodiment, FIG. 2 shows a UV absorption spectrum library of preservative-free controlled drugs comprising the spectra of Fentanyl, Hydromorphone, Ketamine, Lorazepam, Midazolam, and Morphine. It also contains the spectra of typical diluents such as normal saline, lactated ringer's solution, sterile water, plasma-lyte, and dextrose 5% in water. FIG. 3 shows a UV absorption spectrum library of commonly used excipients in controlled drugs comprising the spectra of edetate disodium (EDTA), methylparaben, propylparaben, benzethonium chloride, polyethylene glycol (PEG) 400, propylene glycol, benzyl alcohol, sodium lactate, sodium citrate, citric acid, sodium metabisulfite, chlorobutanol, sodium chloride, and glycine. It can be seen from FIG. 2 and FIG. 3 that the five types of diluents have extremely low UV absorption in the wavelength region of above 230 nm and only a few of the excipients have absorption bands which interfere with that of the controlled drugs in the same wavelength region. Hence by performing spectral analysis in the wavelength region from 230 nm to 400 nm, the major absorption bands of the controlled drugs are covered while the interferences from excipients and diluents are minimized to simplify the analysis procedure.

Figure 4:
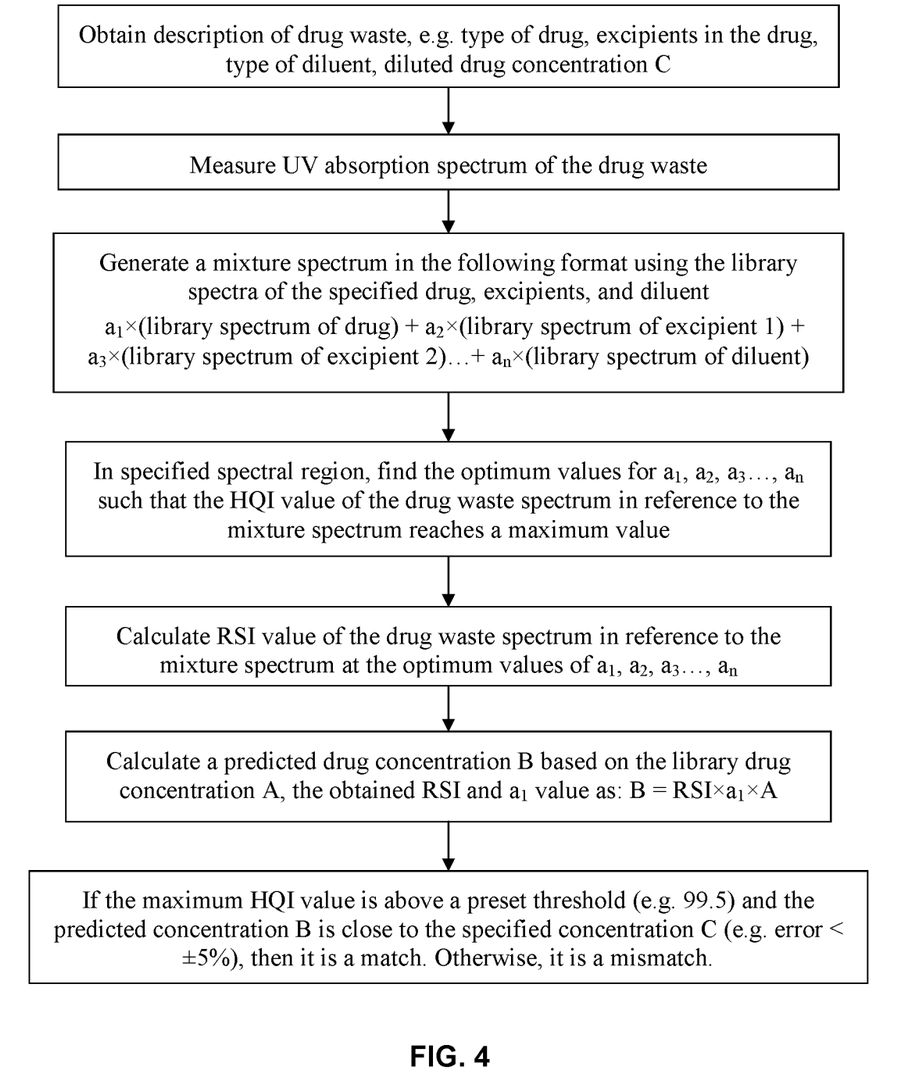
FIG. 4 shows the flow chart of a mixture analysis algorithm for drug waste identification and concentration verification.

In this exemplary embodiment, drug waste identification and concentration verification are performed using a mixture analysis algorithm, which can be implemented on most processors. A flow chart of the algorithm is shown in FIG. 4. Two spectral analysis tools are employed in the algorithm. The Hit Quality Index (HQI) is the correlation coefficient between the sample spectrum and the library spectrum, which is equivalent to measuring the cosine of the angle between two spectra. HQI is calculated by taking the dot product of the sample spectrum and the library spectra, divided by the dot product of the library spectrum with itself and the dot product of the sample spectrum with itself.

$$HQI=(sample \cdot library)^2/(sample \cdot sample)/(library \cdot library) \times 100$$

The resulting correlation coefficient is 100 when the two spectra are in perfect correspondence and 0 when they are orthogonal. The Relative Spectral Intensity (RSI) is used to compare the relative intensity of the sample spectrum and the library spectrum, which is calculated as the ratio of the vector length of the sample spectrum in reference to the library spectrum:

$$RSI=((sample \cdot sample)/(library \cdot library))^{0.5}$$

Since the intensity, i.e., the absorbance value of the measured UV absorption spectrum is proportional to the concentration level of the controlled drug, RSI is actually the ratio of their concentration levels when the sample spectrum and the library spectrum belong to the same type of controlled drug.

In the first step of the analysis procedure, a description of the drug waste is obtained by scanning a barcoded vial or labelled syringe of the drug waste or by manual data entry, which provides information such as the type of controlled drug wasted, excipients in the drug, the type of diluent, the diluted drug concentration C, etc. In the second step, a UV absorption spectrum of the drug waste is measured with the UV spectroscopy apparatus. In the third step, the algorithm generates a mixture spectrum in the following format using the library spectra of the specified drug, excipients, and diluent:

$$a_1 \times (\text{library spectrum of drug}) + a_2 \times (\text{library spectrum of excipient 1}) + a_3 \times (\text{library spectrum of excipient 2}) \ldots + a_n \times (\text{library spectrum of diluent})$$

In the fourth step, the algorithm will find the optimum values for $a_1, a_2, a_3 \ldots, a_n$ such that the HQI value of the drug waste spectrum in reference to the mixture spectrum reaches the maximum value in a specified spectral region. Then the RSI value of the drug waste spectrum in reference to the mixture spectrum is calculated at the optimum values of $a_1, a_2, a_3 \ldots, a_n$ and the predicted drug concentration B is calculated based on the library drug concentration A and the obtained RSI and $a_1$ values as: $B=RSI \times a_1 \times A$. If the maximum HQI value is above a preset threshold (e.g. 99.5) and the predicted concentration B is close to the specified concentration C (e.g. error<±5%), then the content of the drug waste matches with its description. Otherwise, there is a mismatch indicating possible drug diversion. The fourth step of the algorithm can be realized using the approaches such as Generalized Reduced Gradient (GRG) method as proposed by Lasdon et al. It is worth to note that the above disclosed mixture analysis algorithm does not require the concentration information for the excipients, nor does it require the concentration information of the drug waste before dilution.

Figure 5:
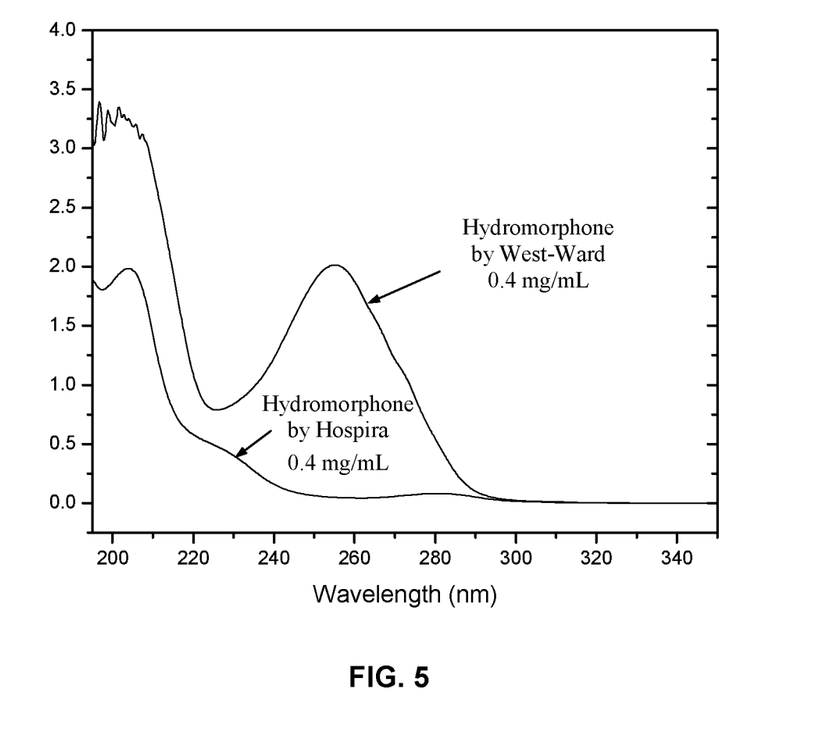
FIG. 5 shows the UV absorption spectra of Hydromorphone samples manufactured by West-Ward pharmaceuticals and Hospira.

The following example further illustrates the drug waste identification and concentration verification process. Here the drug waste is 0.4 mg/mL Hydromorphone manufactured by West-Ward pharmaceuticals. FIG. 5 show a comparison of its spectrum with the spectrum of a Hydromorphone sample manufactured by Hospira, which is also the preservative-free drug sample used to build the spectral library shown in FIG. 2. The West-Ward Hydromorphone shows significantly different spectral shape from the Hospira Hydromorphone because it contains 1.8 mg/mL of methylparaben and 0.2 mg/mL of propylparaben as preservative. Employing the 2 mg/mL Hydromorphone spectrum as shown in FIG. 2 and the methylparaben and propylparaben spectra as shown in FIG. 3, the mixture analysis algorithm produces an HQI value of >99.99 and a predicted concentration of 0.397 mg/mL. The close match confirms the composition and concentration of the drug waste. In this example, the excipients in the drug (i.e., methylparaben and propylparaben) make dominant contribution to the UV absorption for most of the wavelengths. The active ingredient (i.e., Hydromorphone) only makes comparable contribution at wavelengths of <240 nm. Precise prediction of the concentration of the active ingredient is only possible by analyzing the full UV spectrum (e.g., from 230 nm to 400 nm).

The above disclosed mixture analysis algorithm completes drug waste identification and concentration verification in one single step, hence eliminating the need of building concentration calibration curves for each of the controlled drugs. This is made possible by optimizing the optical path length of the cuvette 106, which not only reveals the full UV absorption spectrum of interest but also keeps the measured absorbance at relatively low level hence maintains the linearity of Beer-Lambert law of absorption. It is worth to note that when two excipients have similar spectral shapes, such as methylparaben and propylparaben as shown in FIG. 3, it is possible to use only one of them to perform the mixture analysis without affecting the final result. This will help reduce the time consumption of the analysis. Likewise, when two diluents have similar spectral shapes, such as lactated ringer's solution and plasma-lyte as shown in FIG. 2, their spectra can be used interchangeably to perform the mixture analysis.

Figure 6:
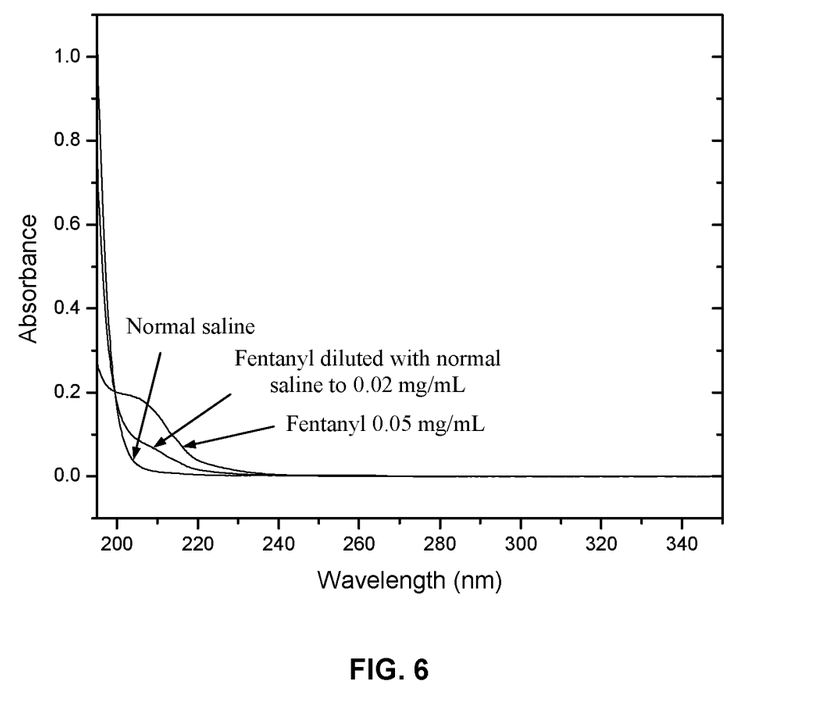
FIG. 6 shows the UV absorption spectra of normal saline, undiluted Fentanyl at 0.05 mg/mL, and diluted Fentanyl with normal saline to 0.02 mg/mL.

For controlled drugs (e.g., Fentanyl and Sufentanil) which are used at low concentration levels under typical clinical settings, it is desirable to utilize even deeper UV wavelength regions (e.g., 195 nm to 230 nm) to perform the spectral analysis. In the following example, the drug waste is Fentanyl diluted with normal saline to a concentration of 0.02 mg/mL. Its spectrum, together with the spectra of normal saline and undiluted Fentanyl at 0.05 mg/mL are shown in FIG. 6. It can be seen that the diluent causes significant change to the spectral shape of the drug. Employing the spectra of normal saline and 0.05 mg/mL Fentanyl as shown in FIG. 2, the mixture analysis algorithm produces an HQI value of >99.99 and a predicted concentration of 0.0203 mg/mL. This verifies the composition and concentration of the drug waste.

In yet another example, the drug waste is actually normal saline but labelled as Fentanyl diluted with normal saline to a concentration of 0.02 mg/mL. The mixture analysis produces an HQI value of 100 and a predicted concentration of 0 mg/mL, indicating that the drug waste is 100% of normal saline and there is possible drug diversion.

Figure 7:
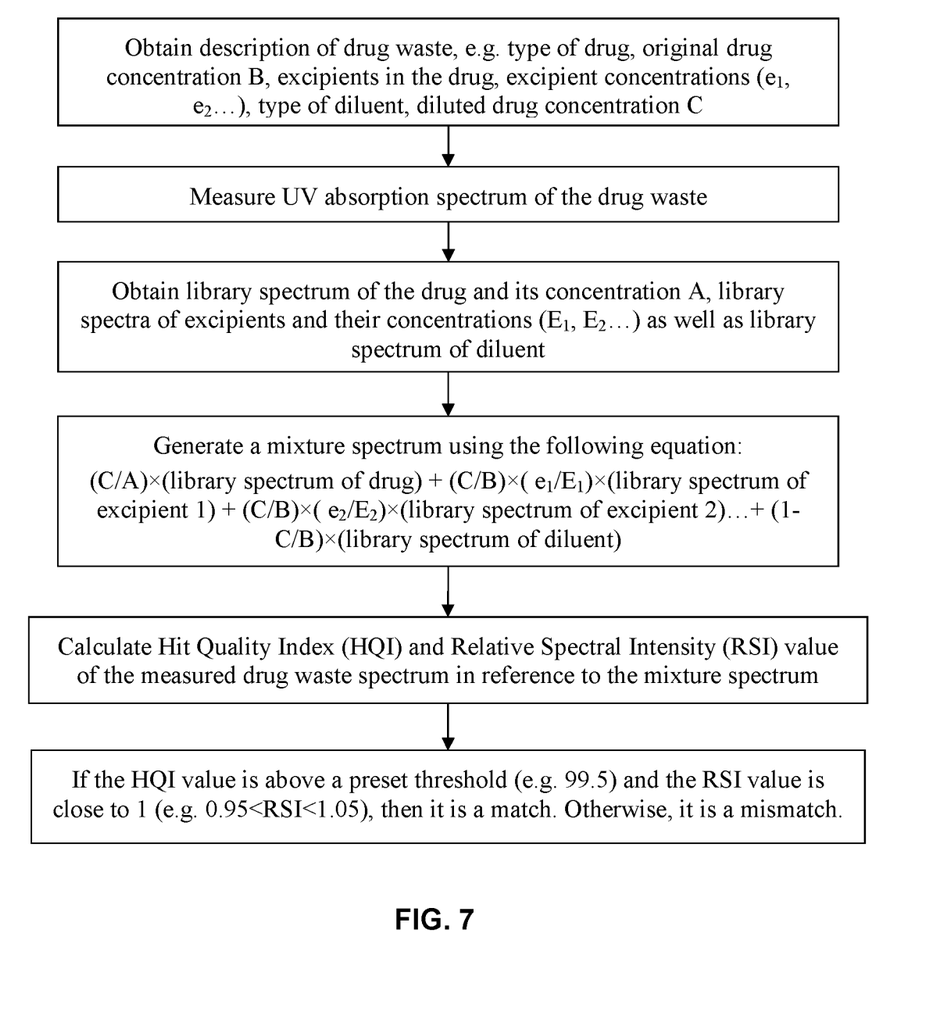
FIG. 7 shows the flow chart of another approach for performing the mixture analysis.

FIG. 7 shows the flow chart of another approach for performing the mixture analysis. This approach requires more information from the description or label of the drug waste, which includes the type of drug, original drug concentration B, excipients in the drug, excipient concentrations ($e_1$, $e_2$ . . . ) in the original drug, type of diluent, and diluted drug concentration C as shown in the first step of the flow chart. In the second step, a UV absorption spectrum of the drug waste is measured with the UV spectroscopy apparatus. In the third step, the following information is obtained from the spectral library, including the library spectrum of the drug and its concentration A, the library spectra of excipients and their concentrations ($E_1$, $E_2$ . . . ) as well as library spectrum of the diluent. In the fourth step, the algorithm generates a mixture spectrum using the following equation:

$$(C/A) \times \text{(library spectrum of drug)} + (C/B) \times (e_1/E_1) \times \text{(library spectrum of excipient 1)} + (C/B) \times (e_2/E_2) \times \text{(library spectrum of excipient 2)} \ldots + (1 - C/B) \times \text{(library spectrum of diluent)}$$

In the fifth step, the Hit Quality Index (HQI) and Relative Spectral Intensity (RSI) value of the measured drug waste spectrum in reference to the mixture spectrum are calculated. If the HQI value is above a preset threshold (e.g. 99.5) and the RSI value is close to 1 (e.g. 0.95<RSI<1.05), then the content of the drug waste matches with its description. Otherwise, there is a mismatch indicating possible drug diversion. The above disclosed approach requires more information from both the description of the drug waste and the spectral library. But it needs less computing power for the processor. Using the same West-Ward Hydromorphone shown in FIG. 5 as an example, the calculated HQI and RSI values of its spectrum in reference to the generated mixture spectrum are 99.9996 and 1.0035, respectively. This indicates that the measured spectrum and the generated mixture spectrum is a close match, hence confirming the composition and concentration of the drug waste.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An apparatus for analyzing a controlled drug waste sample, the apparatus comprising:
   an ultraviolet (UV) light source for producing broadband UV light;
   a sample cell for holding the controlled drug waste sample and receiving the UV light;
   an optical spectrometer for measuring transmitted UV light from the sample cell to obtain a UV absorption spectrum of the controlled drug waste sample;
   a spectral library comprising the UV absorption spectra of preservative-free controlled drugs, commonly used excipients in controlled drugs, and commonly used diluents; and
   a processer configured to generate a mixture spectrum using the library spectra of preservative-free controlled drugs, excipients, and diluents in accordance to a description of the controlled drug waste sample and comparing the spectral shape and spectral intensity of the UV absorption spectrum of the controlled drug waste sample in reference to the mixture spectrum to verify type and concentration of the controlled drug waste sample.

2. The apparatus of claim 1, wherein the optical path length of the sample cell is optimized such that the obtained UV absorption spectrum of the controlled drug waste sample is free of spectral saturation in a predetermined UV wavelength range.

3. The apparatus of claim 2, wherein the predetermined UV wavelength range covers wavelengths down to 230 nm.

4. The apparatus of claim 2, wherein the predetermined UV wavelength range covers wavelengths down to 195 nm.

5. The apparatus of claim 1, wherein the processor predicts a concentration of the controlled drug waste sample by comparing the spectral intensity of its UV absorption spectrum in reference to the mixture spectrum.

6. The apparatus of claim 1, wherein the sample cell comprises two interconnected chambers of different optical path lengths.

7. The apparatus of claim 1, further comprising an additional sample cell of different optical path length.

8. A method for analyzing a controlled drug waste sample, the method comprising the steps of:
   obtaining a description of the controlled drug waste sample;
   obtaining an ultraviolet (UV) absorption spectrum of the controlled drug waste sample;
   providing a spectral library comprising the UV absorption spectra of preservative-free controlled drugs, commonly used excipients in controlled drugs, and commonly used diluents;
   generating a mixture spectrum using the library spectra of preservative-free controlled drugs, excipients, and diluents in accordance to the description of the controlled drug waste sample; and
   comparing the spectral shape and spectral intensity of the UV absorption spectrum of the controlled drug waste sample in reference to the mixture spectrum to verify type and concentration of the controlled drug waste sample.

9. The method of claim 8, wherein the obtained UV absorption spectrum of the controlled drug waste sample is free of spectral saturation in a predetermined UV wavelength range.

10. The method of claim 9, wherein the predetermined UV wavelength range covers wavelengths down to 230 nm.

11. The method of claim 9, wherein the predetermined UV wavelength range covers wavelengths down to 195 nm.

* * * * *